US011467493B2

(12) United States Patent
Lim et al.

(10) Patent No.: US 11,467,493 B2
(45) Date of Patent: Oct. 11, 2022

(54) CHEMICALLY AMPLIFIED PHOTORESIST COMPOSITION AND PHOTORESIST FILM USING THE SAME

(71) Applicant: LG CHEM, LTD., Seoul (KR)

(72) Inventors: Min Young Lim, Daejeon (KR); Yongmi Kim, Daejeon (KR); Ji Hye Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 184 days.

(21) Appl. No.: 16/480,572

(22) PCT Filed: Oct. 25, 2018

(86) PCT No.: PCT/KR2018/012740
§ 371 (c)(1),
(2) Date: Jul. 24, 2019

(87) PCT Pub. No.: WO2019/088569
PCT Pub. Date: May 9, 2019

(65) Prior Publication Data
US 2019/0384176 A1    Dec. 19, 2019

(30) Foreign Application Priority Data

Nov. 1, 2017 (KR) .................. 10-2017-0144766

(51) Int. Cl.
| | | |
|---|---|---|
| G03F 7/039 | (2006.01) | |
| C07D 249/04 | (2006.01) | |
| C08K 5/3472 | (2006.01) | |
| G03F 7/033 | (2006.01) | |

(52) U.S. Cl.
CPC ......... *G03F 7/0392* (2013.01); *C07D 249/04* (2013.01); *C08K 5/3472* (2013.01); *G03F 7/033* (2013.01)

(58) Field of Classification Search
CPC ...... G03F 7/0392; G03F 7/033; G03F 7/0385; G03F 7/038; G03F 7/0757; G03F 7/0755; G03F 7/0047; G03F 7/0007; G03F 7/091; C07D 249/04; C08K 5/3472; Y10S 430/126; Y10S 430/122; Y10S 430/115; H01L 2924/3025; H01L 2924/00; Y10T 428/24802; C09D 133/14; C09D 11/101; C08F 226/06; C08F 226/10
See application file for complete search history.

(56) References Cited

U.S. PATENT DOCUMENTS

| | | | |
|---|---|---|---|
| 2004/0234885 A1 | 11/2004 | Watanabe et al. | |
| 2011/0311809 A1 | 12/2011 | Yamaguchi et al. | |
| 2012/0003436 A1* | 1/2012 | Saie | G03F 7/0047 428/195.1 |
| 2012/0021230 A1 | 1/2012 | Fukatani et al. | |
| 2012/0148514 A1 | 6/2012 | Musa et al. | |
| 2012/0312191 A1* | 12/2012 | Hood | C08F 226/06 106/287.2 |
| 2014/0154624 A1 | 6/2014 | Liu et al. | |
| 2015/0093696 A1 | 4/2015 | Azuma et al. | |
| 2015/0299343 A1 | 10/2015 | Braslau | |
| 2016/0244382 A1 | 8/2016 | Warrender et al. | |

FOREIGN PATENT DOCUMENTS

| | | | |
|---|---|---|---|
| CN | 103946747 A | 7/2014 | |
| CN | 102295896 B | 1/2015 | |
| CN | 104781731 A | 7/2015 | |
| CN | 106674847 A | 5/2017 | |
| EP | 1695987 A1 | 8/2006 | |
| JP | 2002-131906 A | 5/2002 | |
| JP | 2004-347735 A | 12/2004 | |
| JP | 2008-287227 A | 11/2008 | |
| JP | 2009-109590 A | 5/2009 | |
| JP | 2013-041225 A | 2/2013 | |
| JP | 2013-061561 A | 4/2013 | |
| JP | 2013-520458 A | 6/2013 | |
| JP | 2015-068896 A | 4/2015 | |
| JP | WO2013069789 A1 * | 4/2015 | ............. G03F 7/031 |
| JP | 2016-502142 A | 1/2016 | |
| JP | 2016-538231 A | 12/2016 | |
| JP | 2017-129768 A | 7/2017 | |
| KR | 10-2013-0102974 A | 9/2013 | |
| KR | 10-2015-0092164 A | 8/2015 | |
| TW | 201033151 A1 | 9/2010 | |
| WO | 1998-029877 A1 | 7/1998 | |
| WO | 2013-069789 A1 | 5/2013 | |
| WO | 2017-062145 A1 | 4/2017 | |

OTHER PUBLICATIONS

English Translation of JP WO2013/069789 A1; Masaki Obi; Published: Apr. 2, 2015 (Year: 2015).*
Search Report & Written Opinion issued for International Application No. PCT/KR2018/012740 dated Jan. 31, 2019, 13 pages.
Abdelhedi-Miladi, Imen et al.; "UV-Patteming of Ion Conducting Negative Tone Photoresists Using Azide-Functionalized Poly(Ionic Liquid)s"; ACS Macro Letters, 2014, vol. 3, p. 1187-1190.

\* cited by examiner

*Primary Examiner* — Peter L Vajda
*Assistant Examiner* — Richard David Champion
(74) *Attorney, Agent, or Firm* — Rothwell, Figg, Ernst & Manbeck, P.C.

(57) ABSTRACT

A chemically amplified photoresist composition comprising a triazole-based plasticizer and an alkali developable resin, which is capable of minimizing cracking of a photoresist obtained from the composition and improving adhesion to a substrate and sensitivity, and a photoresist film comprising a cured product of the chemically amplified photoresists composition.

13 Claims, No Drawings

CHEMICALLY AMPLIFIED PHOTORESIST COMPOSITION AND PHOTORESIST FILM USING THE SAME

TECHNICAL FIELD

Cross-Reference to Related Application

This application is a 35 U.S.C. § 371 National Phase Entry Application from PCT/KR2018/012740, filed on October 25, 2018, and designating the United States, which claims the benefits of Korean Patent Application No. 10-2017-0144766 filed on November 1, 2017 with the Korean Intellectual Property Office, the disclosures of which are incorporated herein by reference in their entirety.

The present disclosure relates to a chemically amplified photoresist composition and a photoresist film using the same. More specifically, the present disclosure relates to a chemically amplified photoresist composition capable of minimizing cracking of a photoresist obtained from the composition and improving adhesion to a substrate and sensitivity, and a photoresist film using the same.

BACKGROUND OF ART

Photofabrication is the mainstay of microfabrication technology, and packaging technology is constantly changing to a process for manufacturing high-density packages.

In particular, as the number of input/output terminals of semiconductors increases, the use of flip-chip technology has expanded and fan-out wafer level packaging (FOWLP) technology has been introduced. In addition, a TSV (through silicon via) process, which enables direct chip-to-chip connection to minimize signal delay, has expanded, and the demand for bumps has increased. Thus, it is considered important to develop a technology for a bump photoresist which forms the bump.

The bump photoresist requires (i) excellent sensitivity and resolution in a thick film of up to 10 to 100 micrometers, (ii) good pattern performance such as straightness, residue characteristics, footing, and notching characteristics to form metal bumps by a plating process, and (iii) excellent resistance to a plating solution.

Therefore, a chemically amplified photoresist is used to increase sensitivity and resolution in a thick film. Generally, the chemically amplified photoresist composition includes (a) a resin dissociated by an acid to increase solubility in an alkali developer, (b) a photosensitive acid generator (a photoacid generator), (c) an acid diffusion controller, (d) a corrosion inhibitor, and (e) a dissolution inhibitor.

However, in the case of a photoresist obtained from a conventional chemically amplified photoresist composition, cracks are generated on the photoresist as the thickness is increased, and adhesion to a substrate and sensitivity are reduced.

Accordingly, development of a novel chemically amplified photoresist composition capable of improving not only crack resistance of the photoresist but also adhesion to a substrate and sensitivity has been demanded.

DETAILED DESCRIPTION OF THE INVENTION

Technical Problem

The present disclosure is to provide a chemically amplified photoresist composition capable of minimizing cracking of a photoresist obtained from the composition and improving adhesion to a substrate and sensitivity.

In addition, the present disclosure is to provide a photoresist film using the chemically amplified photoresist composition.

Technical Solution

In this disclosure, a chemically amplified photoresist composition including a triazole-based plasticizer represented by the following Chemical Formula 1, and an alkali developable resin, is provided.

[Chemical Formula 1]

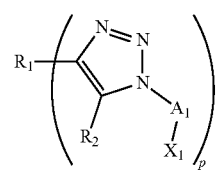

In Chemical Formula 1, $A_1$ is a C1 to C10 alkylene group or a polyalkyleneoxy group represented by the following Chemical Formula 2, $X_1$ is a C1 to C5 alkyl group, a hydroxy group, or a carboxyl group, $R_1$ is an organic functional group having a valence of 1 to 5, $R_2$ is hydrogen, a C1 to C5 alkyl group, a hydroxy group, or a carboxyl group, and p is an integer of 1 to 5,

[Chemical Formula 2]

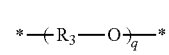

wherein, in Chemical Formula 2, $R_3$ is a C1 to C5 alkylene group, and q is an integer of 1 to 50.

In this disclosure, a photoresist film including a cured product of the chemically amplified photoresist composition is also provided.

The present inventors found that when a chemically amplified photoresist composition prepared by mixing a triazole-based plasticizer having a specific structure as shown in Chemical Formula 1 together with an alkali developable resin is used, crack resistance of the photoresist is increased, and adhesion to a substrate and sensitivity are also improved due to the triazole-based plasticizer represented by the above Chemical Formula 1, and completed this invention.

In particular, the triazole-based plasticizer represented by the above Chemical Formula 1 can easily produce a triazole-based material having various substituents by a click reaction using an azide-based compound and an alkyne-based compound as reaction precursors.

In addition, the triazole-based plasticizer not only improves flexibility and processability of the alkali developable resin as a plasticizer but can also realize an effect of preventing corrosion due to the triazole introduced into the plasticizer structure. Therefore, when the triazole-based plasticizer is used, it is possible to achieve resistance of a plating solution equivalent to that of the case where a corrosion inhibitor is added, without adding a separate corrosion inhibitor.

Hereinafter, the chemically amplified photoresist composition and the photoresist film according to the exemplary embodiments of the present disclosure will be described in more detail.

In the present disclosure, when a part "comprises" or "includes" a component, the part does not exclude other components, but may comprise or include other components unless context states otherwise.

In the present disclosure, examples of substituents are described below, but are not limited thereto.

In the present disclosure, the term "substituted" means that another functional group is bonded in place of a hydrogen atom of the compound, and the position to be substituted is not limited as long as it is a position at which the hydrogen atom is substituted, that is, a position at which the substituent is substitutable. When two or more are substituted, the two or more substituents may be the same or different.

As used herein, the term "substituted or unsubstituted" means that one or more substituent groups selected from the group consisting of deuterium; a halogen group; a cyano group; a nitro group; a hydroxyl group; a carbonyl group; an ester group; an imide group; an amino group; a carboxyl group; a sulfonic acid group; a sulfonamide group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl groups; an aralkenyl group; an alkylaryl group; an arylphosphine group; and a heterocyclic group containing at least one of N, O, and S atoms are substituted or unsubstituted, or a substituent group where two or more substituent groups of the exemplified substituent groups are connected is substituted or unsubstituted. For example, the term "substituent group where two or more substituent groups are connected" may be a biphenyl group. That is, the biphenyl group may be an aryl group, or may be interpreted as a substituent group where two phenyl groups are connected.

In the present disclosure,

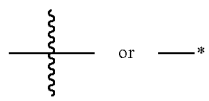

or means a bond connected to another substituent group. A direct bond refers to a case where there is no separate atom at a position represented by L.

In the present disclosure, examples of a halogen group include fluorine, chlorine, bromine, and iodine.

In the present disclosure, the weight average molecular weight refers to a weight average molecular weight measured by a GPC method and calibrated with polystyrene. In the process of measuring the weight average molecular weight, a well-known analyzer, a detector such as a refractive index detector, and an analyzing column may be used. In addition, conventionally applied temperature conditions, solvents, and flow rates may be used. As a specific example of the measurement conditions, a temperature of 30° C., a tetrahydrofuran solvent, and a flow rate of 1 mL/min may be applied.

In the present disclosure, an alkyl group may be a linear chain or a branched chain, and the number of carbon atoms thereof is not particularly limited but is preferably 1 to 40. According to one embodiment, the alkyl group has 1 to 20 carbon atoms. According to another embodiment, the alkyl group has 1 to 10 carbon atoms. According to another embodiment, the alkyl group has 1 to 6 carbon atoms. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present disclosure, the alkenyl group may be a linear chain or a branched chain, and the number of carbon atoms thereof is not particularly limited but is preferably 2 to 40. According to one embodiment, the alkenyl group has 2 to 20 carbon atoms. According to another embodiment, the alkenyl group has 2 to 10 carbon atoms. According to another embodiment, the alkenyl group has 2 to 6 carbon atoms. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

As used herein, the term "direct bond" means that no atom or atomic group exists at the corresponding position, and the groups on both sides are connected by a bond line.

I. Chemically Amplified Photoresist Composition (1) Triazole-Based Plasticizer

The chemically amplified photoresist composition may include a triazole-based plasticizer represented by the following Chemical Formula 1. The triazole-based plasticizer may refer to a triazole derivative compound having a triazole structure in its molecular structure.

[Chemical Formula 1]

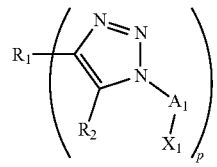

In Chemical Formula 1, $A_1$ is a C1 to C10 alkylene group or a polyalkyleneoxy group represented by the following Chemical Formula 2, $X_1$ is a C1 to C5 alkyl group, a hydroxy group, or a carboxyl group, $R_1$ is an organic functional group having a valence of 1 to 5, $R_2$ is hydrogen, a C1 to C5 alkyl group, a hydroxy group, or a carboxyl group, and p is an integer of 1 to 5,

[Chemical Formula 2]

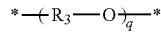

wherein, in Chemical Formula 2, $R_3$ is a C1 to C5 alkylene group, and q is an integer of 1 to 50, 1 to 20, 1 to 10, or 1 to 5. Preferably, $R_3$ of Chemical Formula 2 may be bonded to a nitrogen atom (N) of Chemical Formula 1, and an oxygen atom (O) of Chemical Formula 2 may be bonded to $X_1$ of Chemical Formula 1.

In Chemical Formula 1, $R_1$ is an organic functional group having a valence of 1 to 5, p is an integer of 1 to 5, and preferably, the valence of the organic functional group of $R_1$ is equal to p. The valence of the organic functional group is the number of reaction sites at which the organic functional group can react with other atoms or molecules. That is, in the above Chemical Formula 1, triazole-based functional groups can be bonded at all reaction sites of the organic functional group of $R_1$.

For example, when $R_1$ is a monovalent organic functional group, p is an integer of 1, when $R_1$ is a divalent organic functional group, p is an integer of 2, when $R_1$ is a trivalent organic functional group, p is an integer of 3, when $R_1$ is a tetravalent organic functional group, p is an integer of 4, and when $R_1$ is a pentavalent organic functional group, p is an integer of 5.

More specifically, in the above Chemical Formula 1, $R_1$ may be a monovalent organic functional group represented by the following Chemical Formula 3 or a C1 to C20 alkyl group, and p may be 1.

[Chemical Formula 3]

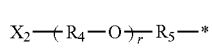

In Chemical Formula 3, $X_2$ is a C1 to C5 alkyl group, a hydroxy group, or a carboxyl group, $R_4$ and $R_5$ are each independently a C1 to C5 alkylene group, and r is an integer of 1 to 10.

More preferably, in the above Chemical Formula 3, $X_2$ may be a carboxyl group, $R_4$ may be a C2 ethylene group, $R_5$ may be a C1 methylene group, and r may be an integer of 5.

In the above Chemical Formula 1, $R_1$ may be a divalent organic functional group represented by the following Chemical Formula 4, and p may be 2.

[Chemical Formula 4]

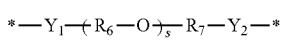

In Chemical Formula 4, $Y_1$ and $Y_2$ are each independently a direct bond, —O—, —CO—, —S—, —C(CH$_3$)$_2$—, —C(CF$_3$)$_2$—, —CONH—, —COO—, —(CH$_2$)$_z$—, —O(CH$_2$)$_z$O—, or —COO—(CH$_2$)$_z$—OCO—, z is an integer of 1 to 10, $R_6$ and $R_7$ are each independently a C1 to C5 alkylene group, and s is an integer of 1 to 50, 1 to 20, or 1 to 10.

More preferably, in Chemical Formula 4, $Y_1$ and $Y_2$ may each independently be —COO—, $R_6$ and $R_7$ may each independently be a C2 ethylene group, and s may be an integer of 5.

Meanwhile, in Chemical Formula 1, (i) $A_1$ is a C1 to C5 alkylene group, and $X_1$ is a carboxyl group, (ii) $A_1$ is a polyalkyleneoxy group represented by the following Chemical Formula 2-1, and $X_1$ is a C1 to C5 alkyl group, or (iii) $A_1$ is a polyalkyleneoxy group represented by the following Chemical Formula 2-1, and $X_1$ is a hydroxyl group.

[Chemical Formula 2-1]

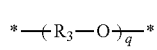

In Chemical Formula 2-1, $R_3$ is a C1 to C3 alkylene group, and q is an integer of 1 to 50, 1 to 20, 1 to 10, or 3 to 5.

More specific examples of the triazole-based plasticizer represented by the above Chemical Formula 1 include a compound represented by the following Chemical Formula 1-1 or 1-2.

[Chemical Formula 1-1]

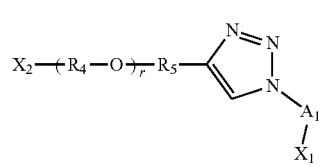

In Chemical Formula 1-1, $A_1$ is a C1 to C5 alkylene group or a polyalkyleneoxy group represented by the Chemical Formula 2-1, $X_1$ is a C1 to C5 alkyl group, a hydroxy group, or a carboxyl group, $X_2$ is a carboxyl group, $R_4$ and $R_5$ are each independently a C1 to C3 alkylene group, and r is an integer of 3 to 7.

[Chemical Formula 1-2]

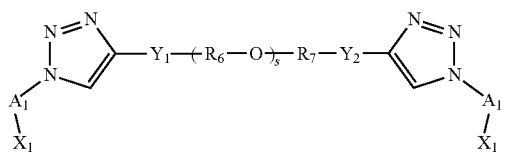

In Chemical Formula 1-2, $A_1$ is a C1 to C5 alkylene group or a polyalkyleneoxy group represented by the Chemical Formula 2-1, $X_1$ is a C1 to C5 alkyl group, a hydroxy group, or a carboxyl group, $X_2$ is a carboxyl group, $Y_1$ and $Y_2$ are each independently —COO—, $R_6$ and $R_7$ are each independently a C1 to C3 alkylene group, and s is an integer of 1 to 10.

Specific examples of the compound represented by Chemical Formula 1-1 include Compounds A-1, A-2, and A-3 described in Synthesis Examples 1 to 3 described below, and specific examples of the compound represented by Chemical Formula 1-2 include Compounds B-1, B-2, and B-3 described in Synthesis Examples 4 to 6 described below.

Meanwhile, the triazole-based plasticizer according to the embodiment of the present disclosure can be synthesized by a chemical reaction (a click reaction) of an azide compound and an alkyne compound.

For example, the triazole-based plasticizer can be synthesized by a mechanism such as Scheme below:

[Scheme]

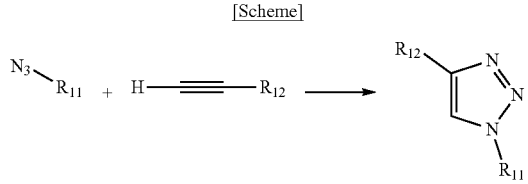

where $R_{11}$ and $R_{12}$ are arbitrary substituents, and various organic or inorganic functional groups can be applied thereto.

(2) Alkali Developable Resin

The chemically amplified photoresist composition of one embodiment may include an alkali developable resin.

According to one embodiment of the present disclosure, the chemically amplified photoresist composition may include a resin dissociated by an acid to increase solubility in an alkali developer (hereinafter referred to as an alkali developable resin), in addition to the above-described triazole-based plasticizer.

The alkali developable resin is not particularly limited as long as it is a polymer resin having an acid group protected by a protecting group. The acid group may be, for example, a carboxyl group, a phenolic hydroxyl group, or the like. The alkali developable resin may be a polymer resin that is well known in the art, and may be, for example, a novolac resin, a hydroxystyrene resin, an acrylic resin, or the like.

Preferably, the alkali developable resin may include at least two selected from the group consisting of a novolac resin, a hydroxystyrene resin, and an acrylic resin. More preferably, it may further include one kind of the novolac resin or the hydroxystyrene resin, while necessarily including the acrylic resin.

More specifically, the alkali developable resin may include: 50 to 90 parts by weight of an acrylic resin; and 10 to 50 parts by weight of a novolac resin or a hydroxystyrene resin, based on 100 parts by weight of the alkali developable resin. Herein, the novolac resin or the hydroxystyrene resin may be mixed in an amount of 30 to 50 parts by weight based on 100 parts by weight of the acrylic resin.

For example, in order to form a stable pattern, it is preferable that the acrylic resin contains 30 to 60 wt % of a repeating unit having a functional group dissociated by an acid in the molecule, based on 100 wt % of the acrylic resin.

The acrylic resin preferably contains 10 to 50 wt % of a repeating unit having a hydrophilic moiety, based on 100 wt % of the acrylic resin for the purpose of wettability with a plating solution or a developer, adhesion to a substrate, and prevention of cracks.

In addition, in order to prevent cracks or swelling in the photoresist pattern during plating, the acrylic resin preferably contains 10 to 50 wt % of a hydrophobic bulky repeating unit capable of imparting plating resistance, based on 100 wt % of the acrylic resin.

Sensitivity and speed of development can be controlled by applying monomers having an acidic group or a hydroxyl group to the formation of the acrylic resin in an amount of 5 to 20 wt %, based on 100 wt % of the acrylic resin. As the monomers, a compound protected by an acid-deprotected group can be applied.

In addition, it is possible to add monomers capable of controlling heat and chemical resistance in the formation of the acrylic resin.

Preferably, the acrylic resin may be a polymer represented by the following Chemical Formula 5.

[Chemical Formula 5]

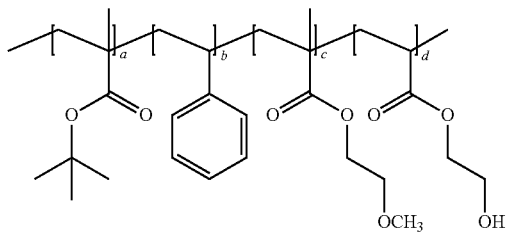

In Chemical Formula 5, a molar ratio of a:b:c:d is 3 to 6:1 to 5:0.5 to 2:1 to 5.

The alkali developable resin may have a weight average molecular weight of 10,000 to 300,000 g/mol, 10,000 to 250,000 g/mol, or 12,000 to 200,000 g/mol, which may be advantageous for forming a stable pattern.

(3) Chemically Amplified Photoresist Composition

The chemically amplified photoresist composition of one embodiment may specifically be a chemically amplified positive-type photoresist composition for a thick film.

The chemically amplified photoresist composition of one embodiment may include 0.1 to 10 parts by weight of the triazole-based plasticizer, based on 100 parts by weight of the alkali developable resin.

The chemically amplified photoresist composition may further include various organic solvents or other additives that are well known in the photoresist field, if necessary.

The organic solvent is included to uniformly dissolve various components, to mix them, and to control viscosity of the photoresist composition. The organic solvent may be applied without limitation as long as it is known to be usable in a positive-type photoresist composition.

For example, the organic solvent may be at least one compound selected from the group consisting of ethylene glycol monomethyl ethyl, ethylene glycol monoethyl ether, ethylene glycol monomethyl ether, ethylene glycol monoacetate, diethylene glycol, diethylene glycol monoethyl ether, diethylene glycol methyl ethyl ether, propylene glycol, propylene glycol monoacetate, propylene glycol methyl ether acetate, toluene, xylene, methyl ethyl ketone, methyl isoamyl ketone, cyclohexanone, dioxane, methyl lactate, ethyl lactate, methyl pyruvate, ethyl pyruvate, methyl methoxypropionate, ethyl ethoxypropionate, N,N-dimethylformamide, N,N-dimethylacetamide, N-methyl-2-pyrrolidone, 3-ethoxyethyl propionate, 2-heptanone, gamma-butyrolactone, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl 3-methoxy-2-methylpropionate, ethyl 3-ethoxypropionate, ethyl 3-methoxy-2-methylpropionate, acetate, and butyl acetate.

The organic solvent may be included in an amount of 5 to 500 parts by weight, 5 to 450 parts by weight, or 5 to 400 parts by weight based on 100 parts by weight of the alkali developable resin. That is, in order to ensure the applicability of the composition, it is preferable that the organic solvent is included in an amount of 5 parts by weight or more based on 100 parts by weight of the alkali developing resin. However, when the organic solvent is included in an excess amount, the viscosity of the composition may be lowered, which may make it difficult to control the thickness of the photoresist. Therefore, it is preferable that the organic solvent is included in an amount of 500 parts by weight or less based on 100 parts by weight of the alkali developable resin.

Examples of the other additives include a photoacid generator, a surfactant, an acid diffusion controller, a photoinitiator, a dissolution inhibitor, and the like. However, as described above, since the chemically amplified photoresist composition of one embodiment uses the triazole-based plasticizer, a separate corrosion inhibitor may not be used.

As the photoinitiator, a compound that is well known in the art may be used without any particular limitation. For example, the photoinitiator may be benzophenone, an aromatic alpha-hydroxy ketone, a benzyl ketal, an aromatic alpha-amino ketone, a phenylglyoxalic acid ester, a monoacylphosphine oxide, a bis-acylphosphine oxide, a trisacylphosphine oxide, an oxime ester derived from an aromatic ketone, an oxime ester of a carbazole type, and the like.

The photoinitiator may be included in an amount of 0.1 to 5 parts by weight based on 100 parts by weight of the alkali developable resin, which may be advantageous for manifesting an appropriate photoinitiating effect.

Further, the photoacid generator may be included in an amount of 0.1 to 10 parts by weight, 0.5 to 10 parts by weight, or 1 to 5 parts by weight, based on 100 parts by weight of the alkali developable resin.

That is, the photoacid generator is preferably included in an amount of 0.1 parts by weight or more based on 100 parts by weight of the alkali developable resin, so that the photoacid generating effect can be fully manifested. However, when the photoacid generator is included in an excess amount, the photosensitivity of the composition may deviate from an appropriate level, and a scum may remain on an exposed part after development. Therefore, it is preferable that the photoacid generator is included in an amount of 10 parts by weight or less based on 100 parts by weight of the alkali developable resin.

The photoacid generator, surfactant, acid diffusion controller, and dissolution inhibitor can be used without limitation, as long as they are commonly used in the positive-type photoresist composition in the art.

The surfactant may be included in an amount of 0.01 to 1 part by weight, 0.05 to 1 part by weight, or 0.05 to 0.5 parts by weight based on 100 parts by weight of the alkali developable resin. When the surfactant is included in an excess amount, wettability and flatness of the composition on the substrate may deviate from an appropriate level. Accordingly, the surfactant is preferably included in an amount of 1 part by weight or less based on 100 parts by weight of the alkali developable resin.

The acid diffusion controller may be included to improve the resist pattern shape, post-exposure stability, and the like. For example, it may be at least one selected from the group consisting of triethylamine, tripropyl amine, tribenzyl amine, trihydroxyethyl amine, and ethylene diamine.

II. Photoresist Film

According to another embodiment of the present disclosure, a photoresist film including a cured product of the chemically amplified photoresist composition of the above-described embodiment is provided.

Specifically, the photoresist film may be formed by a method including the steps of: applying and drying the chemically amplified photoresist composition of one embodiment; and exposing and developing the chemically amplified photoresist composition.

More specifically, an example of the preparation method of the photoresist film is as follows. The photoresist composition of the above-describe embodiment was spin-coated on a 4-inch Si wafer coated with copper (Cu) to a thickness of about 2000 Å, and dried at 120° C. for 4 minutes to form a photoresist layer of about a 50 μm thickness. The wafer was exposed using an i-line stepper (equipped with a photomask having hole patterns of about a 10, 20, 30, 40, and 50 μm size). The exposed wafer was dried at 100° C. for 3 minutes, and then developed for 300 seconds using a developing solution (about 2.38 wt % tetramethylammonium hydroxide aqueous solution).

The photoresist film of the present embodiment can exhibit excellent sensitivity, developability, and adhesion at a low exposure dose, and can exhibit excellent crack resistance even without a separate corrosion inhibitor (NIT).

ADVANTAGEOUS EFFECTS

According to the present disclosure, it is possible to provide a chemically amplified photoresist composition capable of minimizing cracking of a photoresist obtained from the composition and improving adhesion to a substrate and sensitivity, and a photoresist film using the same.

DETAILED DESCRIPTION OF THE EMBODIMENTS

The invention will be described in more detail in the following examples. However, these examples are for illustrative purposes only, and the invention is not intended to be limited by these examples.

SYNTHESIS EXAMPLES: SYNTHESIS OF PLASTICIZER

Synthesis Example 1

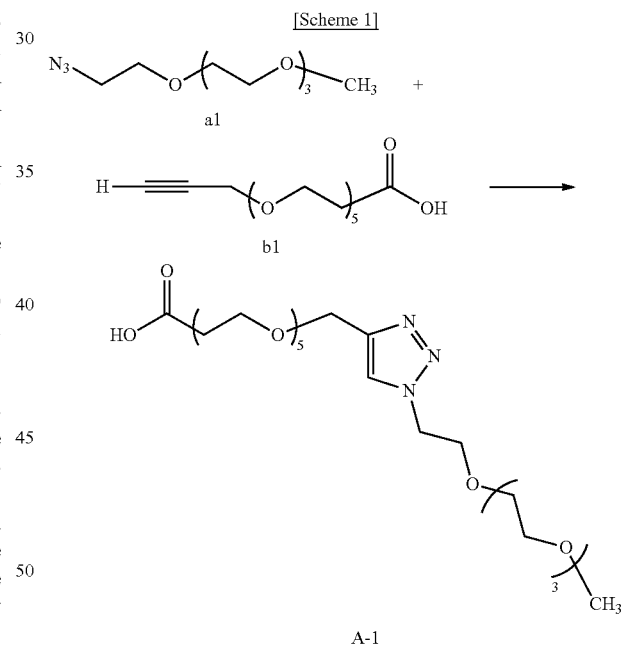

Compound A-1 was obtained by a click reaction between Compound a1 and Compound b1.

Specifically, 1.0 equiv. of Compound a1 and 1.0 equiv. of Compound b1 were dissolved in chloroform, and then a preliminarily prepared catalyst solution (CuBr/PMDETA=1/1 mol/mol, wherein PMDETA is N,N,N',N'',N''-pentamethyldiethylenetriamine) was added thereto in an amount of 0.05 equiv. based on CuBr at room temperature, followed by stirring for 12 hours. The reaction mixture was washed with water and HCl (1 N), and then an organic layer was concentrated and purified by column chromatography to obtain 21 g of Compound A-1 (60% yield).

Synthesis Example 2

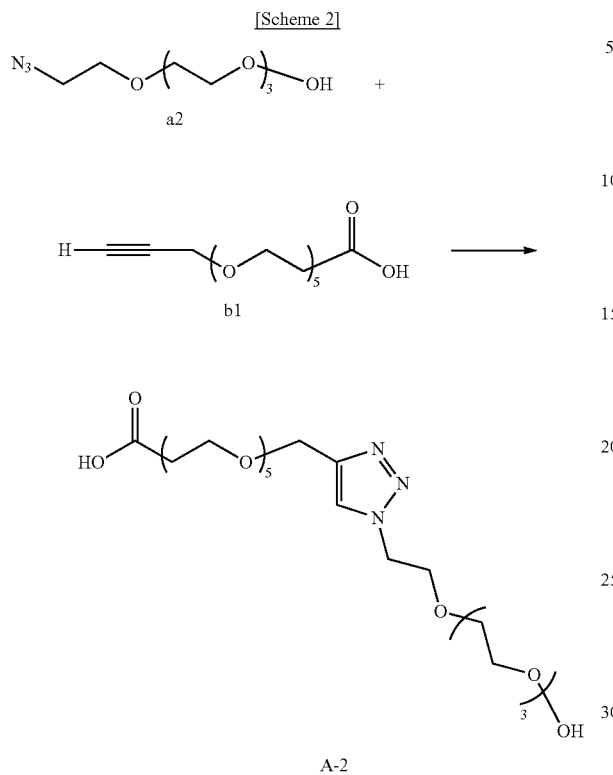

Compound A-2 was obtained by a click reaction between Compound a2 and Compound b1.

Specifically, 1.0 equiv. of Compound a2 and 1.0 equiv. of Compound b1 were dissolved in chloroform, and then a preliminarily prepared catalyst solution (CuBr/PMDETA=1/1 mol/mol, wherein PMDETA is N,N,N',N'',N''-pentamethyldiethylenetriamine) was added thereto in an amount of 0.05 equiv. based on CuBr at room temperature, followed by stirring for 12 hours. The reaction mixture was washed with water and HCl (1 N), and then an organic layer was concentrated and purified by column chromatography to obtain 21 g of Compound A-2 (60% yield).

Synthesis Example 3

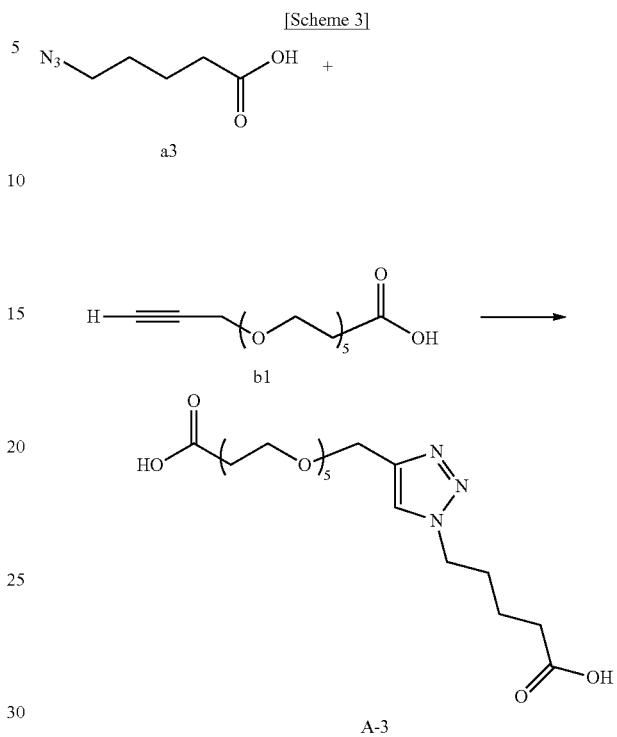

Compound A-3 was obtained by a click reaction between Compound a3 and Compound b1.

Specifically, 1.0 equiv. of Compound a3 and 1.0 equiv. of Compound b1 were dissolved in chloroform, and then a preliminarily prepared catalyst solution (CuBr/PMDETA=1/1 mol/mol, wherein PMDETA is N,N,N',N'',N''-pentamethyldiethylenetriamine) was added thereto in an amount of 0.05 equiv. based on CuBr at room temperature, followed by stirring for 12 hours. The reaction mixture was washed with water and HCl (1 N), and then an organic layer was concentrated and purified by column chromatography to obtain 21 g of Compound A-3 (60% yield).

Synthesis Example 4

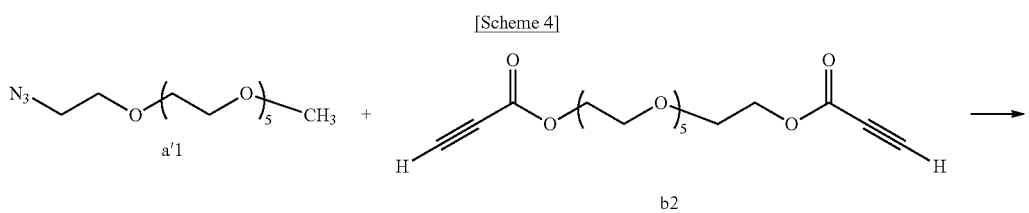

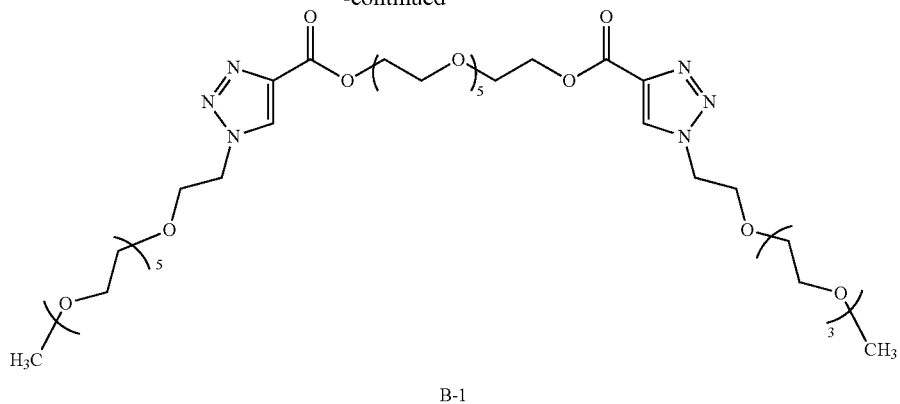

B-1

Compound B-1 was obtained by a click reaction between Compound a'1 and Compound b2.

Specifically, 1.0 equiv. of Compound a'1 and 1.0 equiv. of Compound b2 were dissolved in chloroform, and then a preliminarily prepared catalyst solution (CuBr/PMDETA=1/1 mol/mol, wherein PMDETA is N,N,N',N'',N-pentamethyldiethylenetriamine) was added thereto in an amount of 0.05 equiv. based on CuBr at room temperature, followed by stirring for 12 hours. The reaction mixture was washed with water and HCl (1 N), and then an organic layer was concentrated and purified by column chromatography to obtain 21 g of Compound B-1 (60% yield).

Synthesis Example 5

[Scheme 5]

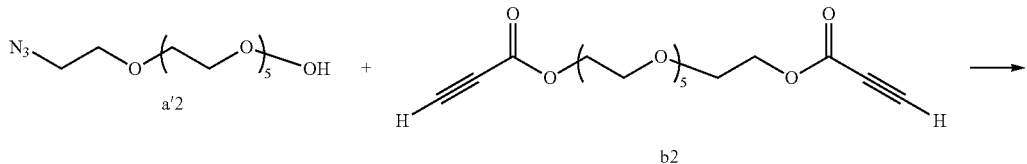

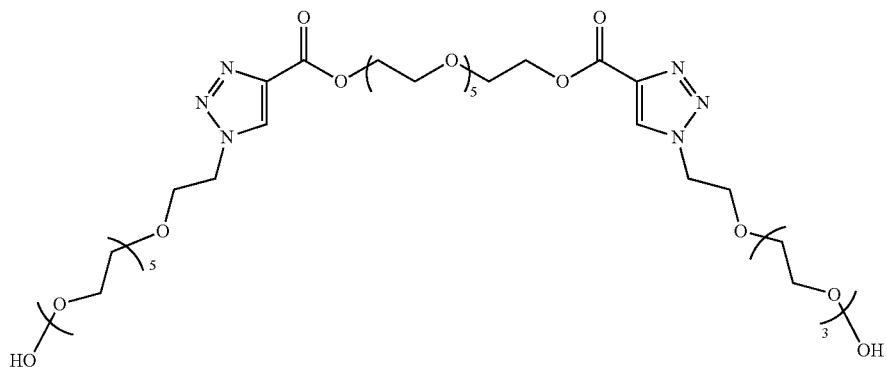

B-2

Compound B-2 was obtained by a click reaction between Compound a'2 and Compound b2.

Specifically, 1.0 equiv. of Compound a'2 and 1.0 equiv. of Compound b2 were dissolved in chloroform, and then a preliminarily prepared catalyst solution (CuBr/PMDETA=1/1 mol/mol, wherein PMDETA is N,N,N',N'',N''-pentamethyldiethylenetriamine) was added thereto in an amount of 0.05 equiv. based on CuBr at room temperature, followed by stirring for 12 hours. The reaction mixture was washed with water and HCl (1 N), and then an organic layer was concentrated and purified by column chromatography to obtain 21 g of Compound B-2 (60% yield).

Synthesis Example 6

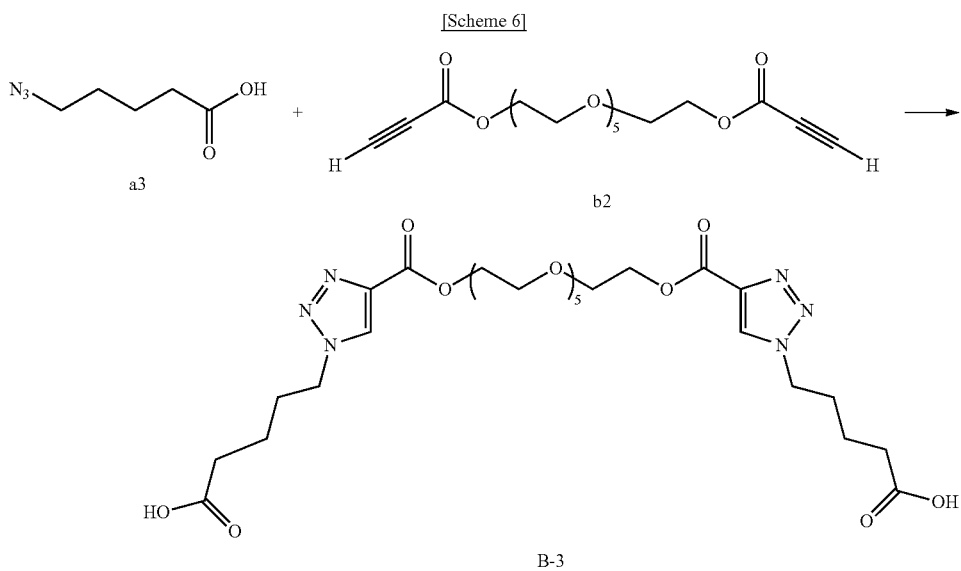

Compound B-3 was obtained by a click reaction between Compound a3 and Compound b2.

Specifically, 1.0 equiv. of Compound a3 and 1.0 equiv. of Compound b2 were dissolved in chloroform, and then a preliminarily prepared catalyst solution (CuBr/PMDETA=1/1 mol/mol, wherein PMDETA is N,N,N',N'',N''-pentamethyldiethylenetriamine) was added thereto in an amount of 0.05 equiv. based on CuBr at room temperature, followed by stirring for 12 hours. The reaction mixture was washed with water and HCl (1 N), and then an organic layer was concentrated and purified by column chromatography to obtain 21 g of Compound B-3 (60% yield).

EXAMPLES AND COMPARATIVE EXAMPLES: PREPARATION OF CHEMICALLY AMPLIFIED PHOTORESIST COMPOSITION

Examples 1 to 8

The components shown in Table 1 below were mixed to prepare chemically amplified photoresist compositions of Examples 1 to 8, respectively.

Specifically, the photoresist composition was prepared by mixing 100 g of an alkali developable resin (R1-R3), 5 g of a plasticizer (A-1, A-2, A-3, B-1, B-2, B-3), and 10 g of an organic solvent (PGMEA).

In the following Table 1, the components applied to the above examples are as follows.

[R1] m,p-cresol novolac resin (Mw 12,000 g/mol, ADR 500 Å/s)

[R2] Acetal protected polyhydroxystyrene (PHS) resin (Mw 15,300 g/mol, substitution rate 40%)

[R3] Acrylic resin (Mw 50,000 g/mol)

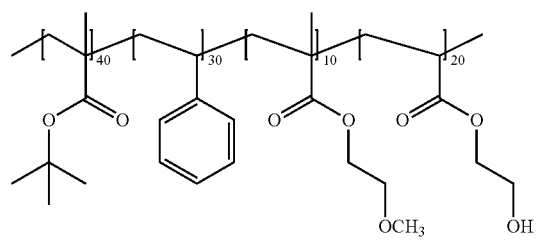

[A-1] Plasticizer (Compound A-1 according to Synthesis Example 1)

[A-2] Plasticizer (Compound A-2 according to Synthesis Example 2)

[A-3] Plasticizer (Compound A-3 according to Synthesis Example 3)

[B-1] Plasticizer (Compound B-1 according to Synthesis Example 4)

[B-2] Plasticizer (Compound B-2 according to Synthesis Example 5)

[A-3] Plasticizer (Compound B-3 according to Synthesis Example 6)

Comparative Examples 1 to 3

The components shown in Table 1 below were mixed to prepare chemically amplified photoresist compositions of Comparative Examples 1 to 3, respectively.

Specifically, a photoresist composition was prepared by mixing 100 g of an alkali developable resin (R1-R3), 1 g of a corrosion inhibitor (benzotriazole, BTA), and 10 g of an organic solvent (PGMEA).

TABLE 1

| | R1 | R2 | R3 | A-1 | A-2 | A-3 | B-1 | B-2 | B-3 | BTA |
|---|---|---|---|---|---|---|---|---|---|---|
| Ex. 1 | 30 | — | 70 | 5 | — | — | — | — | — | — |
| Ex. 2 | 30 | — | 70 | — | 5 | — | — | — | — | — |
| Ex. 3 | 30 | — | 70 | — | — | 5 | — | — | — | — |
| Ex. 4 | 30 | — | 70 | — | — | — | 5 | — | — | — |
| Ex. 5 | 30 | — | 70 | — | — | — | — | 5 | — | — |
| Ex. 6 | 30 | — | 70 | — | — | — | — | — | 5 | — |
| Ex. 7 | — | 30 | 70 | 5 | — | — | — | — | — | — |
| Ex. 8 | — | 30 | 70 | — | — | — | 5 | — | — | — |
| Comp. Ex. 1 | 30 | — | 70 | — | — | — | — | — | — | 1 |
| Comp. Ex. 2 | — | 30 | 70 | — | — | — | — | — | — | 1 |
| Comp. Ex. 3 | — | — | 100 | — | — | — | — | — | — | 1 |

The content of the components listed in the Table 1 is based on the solid content. The sum of the alkali developable resin is 100 parts by weight, and the photoacid generator and the corrosion inhibitor are based on 100 parts by weight of the alkali developable resin.

Experimental Examples

Physical properties of the photoresist composition were evaluated in the following manner by using the respective photoresist compositions according to the examples and comparative examples, and the results are shown in Table 2 below.

(1) Sensitivity (Exposure Dose, mJ/cm$^2$)

The photoresist compositions prepared in Examples 1 to 8 and Comparative Examples 1 to 3 were spin-coated on a glass substrate and dried on a hot plate at 120° C. for 2 minutes. Then, it was exposed using a step mask, further dried on the hot plate at 100° C. for 2 minutes, and then developed in an aqueous solution of tetramethylammonium hydroxide (TMAH). The exposure dose of the step mask pattern and the photoresist (PR) pattern with the same CD (Critical Dimension) size was evaluated as sensitivity.

(2) Occurrence of Footing at Lower Part of Pattern

The photoresist compositions prepared in Examples 1 to 8 and Comparative Examples 1 to 3 were spin-coated on a glass substrate and dried on a hot plate at 120° C. for 2 minutes. Then, they were exposed using a step mask, further dried on the hot plate at 100° C. for 2 minutes, and then developed in an aqueous solution of tetramethylammonium hydroxide (TMAH). A reduced value of the hole diameter from the top to the bottom of the thick film resist pattern was evaluated as a footing length. The footing property of PR was evaluated based on the following criteria.

◎: The footing length of more than 0 nm and below 200 nm

○: The footing length of more than 200 nm and below 500 nm

Δ: The footing length of more than 500 nm and below 1 μm

X: The footing length of more than 1 μm (3) Adhesion

The photoresist compositions prepared in Examples 1 to 8 and Comparative Examples 1 to 3 were spin-coated on a glass substrate and dried on a hot plate at 120° C. for 2 minutes. Then, they were exposed using a step mask, further dried on the hot plate at 100° C. for 2 minutes, and then developed in an aqueous solution of tetramethylammonium hydroxide (TMAH) to prepare a resist pattern. Herein, whether the resist pattern was scratched or not was observed and used as an index of the adhesion. The adhesion was evaluated based on the following criteria.

◎: a 5B rating on ASTM D3359-97 Cross-Cut Tape test

○: a 4B rating on ASTM D3359-97 Cross-Cut Tape test

Δ: a 3B rating on ASTM D3359-97 Cross-Cut Tape test

X: a 2B rating on ASTM D3359-97 Cross-Cut Tape test (4) Crack Resistance

The photoresist compositions prepared in Examples 1 to 8 and Comparative Examples 1 to 3 were spin-coated on a glass substrate to a thickness of 6 μm and dried on a hot plate at 120° C. for 2 minutes. Then, they were exposed using a step mask, further dried on the hot plate at 100° C. for 2 minutes, and then developed in an aqueous solution of tetramethylammonium hydroxide (TMAH) to prepare a resist pattern. Herein, whether or not cracks were generated in the resist pattern was observed and used as an index of the crack resistance. The crack resistance was evaluated based on the following criteria.

◎: When left in yellow room after development, cracks occurred after 3 weeks.

○: When left in yellow room after development, cracks occurred after 2 weeks.

Δ: When left in yellow room after development, cracks occurred after 1 week.

X: When left in yellow room after development, cracks occurred after 3 days.

TABLE 2

| | Sensitivity (mJ/cm$^2$) | Footing | Adhesion | Crack resistance |
|---|---|---|---|---|
| Ex. 1 | 340 | ○ | ○ | ○ |
| Ex. 2 | 280 | ○ | ◎ | ○ |
| Ex. 3 | 210 | ○ | ○ | ○ |
| Ex. 4 | 260 | ○ | ◎ | ○ |
| Ex. 5 | 310 | ◎ | ◎ | ◎ |
| Ex. 6 | 180 | ◎ | ◎ | ◎ |
| Ex. 7 | 330 | ◎ | ◎ | ○ |
| Ex. 8 | 310 | ◎ | ◎ | ○ |
| Comp. Ex. 1 | 870 | X | ○ | X |
| Comp. Ex. 2 | 790 | Δ | Δ | X |
| Comp. Ex. 3 | 990 | Δ | X | X |

Referring to Table 2 above, the photoresist compositions according to the examples showed excellent sensitivity, developability, and adhesion at a low exposure dose, and were confirmed to exhibit excellent crack resistance even without a separate corrosion inhibitor.

The invention claimed is:
1. A chemically amplified photoresist composition comprising:
   a triazole-based plasticizer represented by the following Chemical Formula 1; and
   an alkali developable resin,

[Chemical Formula 1]

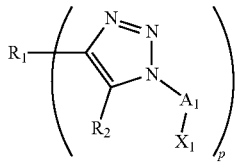

wherein, in Chemical Formula 1,
(i) $A_1$ is a $C_1$ to $C_5$ alkylene group, and $X_1$ is a carboxyl group,
(ii) $A_1$ is a polyalkyleneoxy group represented by the following Chemical Formula 2-1, and $X_1$ is a $C_1$ to $C_5$ alkyl group, or
(iii) $A_1$ is a polyalkyleneoxy group represented by the following Chemical Formula 2-1, and $X_1$ is a hydroxyl group,
$R_1$ is an organic functional group having a valence of 1 to 5,
$R_2$ is hydrogen, a C1 to C5 alkyl group, a hydroxy group, or a carboxyl group, and
p is an integer of 1 to 5,

[Chemical Formula 2-1]

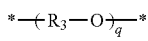

wherein, in Chemical Formula 2-1, $R_3$ is a C1 to C3 alkylene group, and q is an integer of 1 to 50.

2. The chemically amplified photoresist composition according to claim 1,
wherein, in Chemical Formula 1,
$R_1$ is a monovalent organic functional group represented by the following Chemical Formula 3 or a C1 to C20 alkyl group, and p is 1,

[Chemical Formula 3]

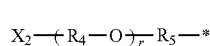

wherein, in Chemical Formula 3,
$X_2$ is a C1 to C5 alkyl group, a hydroxy group, or a carboxyl group,
$R_4$ and $R_5$ are each independently a C1 to C5 alkylene group, and
r is an integer of 1 to 10.

3. The chemically amplified photoresist composition according to claim 1,
wherein, in Chemical Formula 1,
$R_1$ is a divalent organic functional group represented by the following Chemical Formula 4, and p is 2,

[Chemical Formula 4]

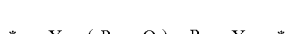

wherein, in Chemical Formula 4,
$Y_1$ and $Y_2$ are each independently a direct bond, —O—, —CO—, —S—, —C(CH$_3$)$_2$—, —C(CF$_3$)$_2$—, —CONH—, —COO—, —(CH$_2$)$_z$—, —O(CH$_2$)$_z$O—, or —COO—(CH$_2$)$_z$—OCO—,
z is an integer of 1 to 10,
$R_6$ and $R_7$ are each independently a C1 to C5 alkylene group, and
s is an integer of 1 to 50.

4. The chemically amplified photoresist composition according to claim 1,
wherein the triazole-based plasticizer is a compound represented by the following Chemical Formula 1-1:

[Chemical Formula 1-1]

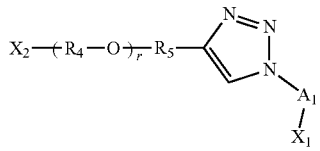

wherein, in Chemical Formula 1-1,
$A_1$ is a C1 to C5 alkylene group or a polyalkyleneoxy group represented by the following Chemical Formula 2-1,
$X_1$ is a C1 to C5 alkyl group, a hydroxy group, or a carboxyl group,
$X_2$ is a carboxyl group, and
$R_4$ and $R_5$ are each independently a C1 to C3 alkylene group, and
r is an integer of 3 to 7,

[Chemical Formula 2-1]

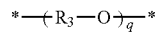

wherein, in Chemical Formula 2-1, $R_3$ is a C1 to C3 alkylene group, and q is an integer of 1 to 50.

5. The chemically amplified photoresist composition according to claim 1,
wherein the triazole-based plasticizer is a compound represented by the following Chemical Formula 1-2:

[Chemical Formula 1-2]

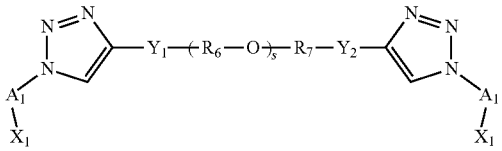

wherein, in Chemical Formula 1-2,
$A_1$ is a C1 to C5 alkylene group or a polyalkyleneoxy group represented by the following Chemical Formula 2-1,
$X_1$ is a C1 to C5 alkyl group, a hydroxy group, or a carboxyl group,
$X_2$ is a carboxyl group,
$Y_1$ and $Y_2$ are each independently —COO—,
$R_6$ and $R_7$ are each independently a C1 to C3 alkylene group, and s is an integer of 1 to 50,

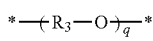
[Chemical Formula 2-1]

wherein, in Chemical Formula 2-1, $R_3$ is a C1 to C3 alkylene group, and q is an integer of 1 to 50.

6. The chemically amplified photoresist composition according to claim 1,
wherein 0.1 to 10 parts by weight of the triazole-based plasticizer is included based on 100 parts by weight of the alkali developable resin.

7. The chemically amplified photoresist composition according to claim 1,
wherein the alkali developable resin comprises at least two selected from the group of a novolac resin, a hydroxystyrene resin, and an acrylic resin.

8. The chemically amplified photoresist composition according to claim 7,
wherein the acrylic resin is represented by the following Chemical Formula 5:

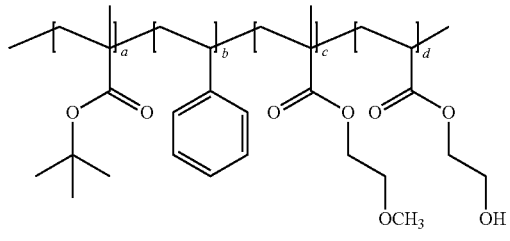
[Chemical Formula 5]

wherein, in Chemical Formula 5,
a molar ratio of a:b:c:d is 3 to 6:1 to 5:0.5 to 2:1 to 5.

9. The chemically amplified photoresist composition according to claim 7, the alkali developable resin comprises the acrylic resin and at least one selected from the group of the novolac resin and the hydroxystyrene resin.

10. The chemically amplified photoresist composition according to claim 9,
wherein the alkali developable resin comprises 50 to 90 parts by weight of an acrylic resin, and 10 to 50 parts by weight of a novolac resin or a hydroxystyrene resin, based on 100 parts by weight of the alkali developable resin.

11. The chemically amplified photoresist composition according to claim 1,
wherein the alkali developable resin comprises 50 to 90 parts by weight of an acrylic resin, and 10 to 50 parts by weight of a novolac resin or a hydroxystyrene resin, based on 100 parts by weight of the alkali developable resin.

12. The chemically amplified photoresist composition according to claim 1,
wherein the alkali developable resin has a weight average molecular weight (measured by GPC) of 10,000 g/mol to 300,000 g/mol.

13. A photoresist film comprising a cured product of the chemically amplified photoresist composition according to claim 1.

* * * * *